United States Patent
Tan Hehir et al.

(10) Patent No.: US 10,744,212 B2
(45) Date of Patent: Aug. 18, 2020

(54) TOPICAL APPLICATION OF NERVE LABELING DYES FOR IMAGE-GUIDED SURGERY

(71) Applicant: GENERAL ELECTRIC COMPANY, Schenectady, NY (US)

(72) Inventors: Cristina Abucay Tan Hehir, Niskayuna, NY (US); Tiberiu Mircea Siclovan, Rexford, NY (US); Victoria Eugenia Cotero, Watervliet, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1193 days.

(21) Appl. No.: 15/069,198

(22) Filed: Mar. 14, 2016

(65) Prior Publication Data

US 2017/0258941 A1    Sep. 14, 2017

(51) Int. Cl.

| | | |
|---|---|---|
| *A61K 49/00* | (2006.01) | |
| *A61B 5/00* | (2006.01) | |
| *A61K 9/00* | (2006.01) | |
| *A61K 47/10* | (2017.01) | |
| *A61K 47/22* | (2006.01) | |
| *A61K 47/32* | (2006.01) | |

(52) U.S. Cl.
CPC ........ *A61K 49/0021* (2013.01); *A61B 5/0068* (2013.01); *A61B 5/0071* (2013.01); *A61B 5/0084* (2013.01); *A61K 9/0014* (2013.01); *A61K 47/10* (2013.01); *A61K 47/22* (2013.01); *A61K 47/32* (2013.01); *A61K 49/0071* (2013.01)

(58) Field of Classification Search
None
See application file for complete search history.

(56) References Cited

U.S. PATENT DOCUMENTS

| | | |
|---|---|---|
| 8,617,515 B2 | 12/2013 | Tan Hehir et al. |
| 8,658,129 B2 | 2/2014 | Zhang et al. |
| 8,977,331 B2 | 3/2015 | Kim et al. |
| 9,040,019 B2 | 5/2015 | Siclovan et al. |
| 2007/0122344 A1 | 5/2007 | Golijanin |
| 2008/0194970 A1 | 8/2008 | Steers et al. |
| 2008/0317679 A1 | 12/2008 | Tamarkin et al. |
| 2010/0310456 A1 | 12/2010 | Siclovan et al. |
| 2011/0142759 A1 | 6/2011 | Zhang et al. |
| 2014/0154178 A1 | 6/2014 | Siclovan et al. |

FOREIGN PATENT DOCUMENTS

| | | |
|---|---|---|
| WO | 9204916 A2 | 4/1992 |
| WO | 2010/141704 A2 | 12/2010 |

OTHER PUBLICATIONS

Cotero, V.E, et al, "Intraoperative Fluorescence Imaging of Peripheral and Central Nerves Through a Myelin-Selective Contrast Agent," Molecular Imaging and Biology, vol. 14, Issue 6, pp. 708-717 (Dec. 2012).
Notice of Acceptance issued in connection with corresponding AU Application No. 2017201729 dated Dec. 10, 2018.
Office Action issued in connection with corresponding RU Application No. 2017108177 dated Dec. 10, 2018.
Cotero et al, "Intraoperative Fluorescence Imaging of Peripheral and Central Nerves Through a Myelin-Selective Contrast Agent", Molecular Imaging and Biology, vol. 14, Issue 6, pp. 708-717, Dec. 2012.
Cotero et al., "Improved Intraoperative Visualization of Nerves through a Myelin-Binding Fluorophore and Dual-Mode Laparoscopic Imaging", PLOS One, vol. 10, Issue 6, pp. 1-18, Jun. 2015.
Office Action issued in connection with corresponding RU Application No. 2017108177 dated May 3, 2018.
Siclovan, M. T., et al., "Fluorescence phenomena in nerve-labeling styryl-type dyes," Journal of Photochemistry and Photobiology A: Chemistry, vol. 316, pp. 104-116 (2016).
Extended European Search Report and Opinion issued in connection with corresponding EP Application No. 17159417.9 dated Sep. 1, 2017.

*Primary Examiner* — Jennifer Lamberski
(74) *Attorney, Agent, or Firm* — Fletcher Yoder, P.C.

(57) ABSTRACT

The present invention relates to a topical agent that binds specifically to myelin basic protein and its method of use and determining myelination in the subject by detecting the agent present in the subject. A kit containing the agent or its derivatives for use in detecting myelin basic protein is also provided.

24 Claims, 7 Drawing Sheets

White Light

Fluorescence

White Light

Fluorescence

Control

Ib

Ic

Id

Ie

If

TOPICAL APPLICATION OF NERVE LABELING DYES FOR IMAGE-GUIDED SURGERY

FEDERALLY SPONSORED RESEARCH & DEVELOPMENT

This invention was made with government support under contract number R01 EB011872 awarded by National Institutes of Health through National Institute of Biomedical Imaging and Bioengineering. The government has certain rights in the invention.

BACKGROUND

This invention relates to fluorescence-guided nerve imaging during surgery, specifically to the field of intraoperative topical administration of myelin basic protein (MBP) nerve imaging contrast agents. Also provided are pharmaceutical formulations for topical administration of the contrast agents to allow for intraoperative nerve identification.

Unintended nerve injury is a leading cause of morbidity associated with many lifesaving surgical procedures. Complications arising from these injuries are dependent on the severity and location of the nerve injury and often result in symptoms that negatively impact the patient's quality of life, such as loss of function and/or sensation, muscle atrophy, paralysis, and chronic neuropathy. Cancer surgery requiring radical resection in the abdomen and pelvis is of particular importance, as many small nerves are involved in sensory, motor, and autonomic functions. In colorectal and gynecologic surgery, preservation of autonomic nerves that control the bladder and bowel is of utmost importance after achieving cancer control. In the field of urology, outcome studies following radical prostatectomy showed that urinary and sexual dysfunction were common even 5 years following the procedure as a result of nerve damage. These nerves in the neurovascular bundle are often difficult to visualize during surgery, even under magnification, due to their intricacy, size, and anatomic variations among individuals. The causes of nerve injury are varied but often results from limited ability to distinguish nerve fibers from the surrounding tissue; they can be mistaken for vessels, or they can be resected along with the targeted malignancy because of their proximity. Current nerve-sparing techniques rely primarily upon anatomic landmark identification, which is highly dependent on the surgeon's experience.

Intraoperative identification of nerves has been successfully demonstrated using fluorescence image-guided surgery in preclinical studies using systemically injected contrast agents (cite our patents and publications). Following intravenous (IV) injection in animals, sufficient time is needed to allow the contrast agent to distribute into the whole body, target the specific protein, and clear from the non-target areas. Since fluorescence-guided surgery was first used, few targeted optical agents have been tested in humans. There is a barrier to clinical translation because of the regulatory oversight on testing systemically administered contrast agents into human. Topical administration has the potential to lower the cost of the clinical development program, making the transition to human studies more feasible.

Compared to systemic delivery of contrast agent, the topical application has many potential advantages. It could potentially limit the possibility of systemic absorption and toxicity thereby enhancing the safety profile of the contrast agent. It could produce high and sustained dose of the contrast agent at the surgical site, where intraoperative visualization is most needed, while limiting the concentration elsewhere. It would also allow the surgeons to control the timing of topical application, so that they can apply it at the surgical site when needed.

Thus, a need for a topical agent that can label nerves exists.

BRIEF DESCRIPTION

Provided herein are topical agents capable of binding myelin-basic protein.

In one embodiment, the pharmaceutical agent comprising a compound of Formula I or a salt thereof, wherein Formula I is:

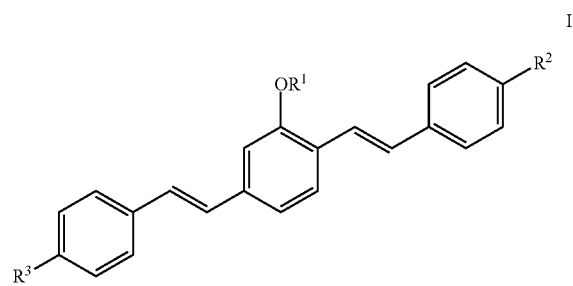

$R^1$ is an alkyl group, $R^2$ is an electron donating group, and $R^3$ is an electron withdrawing group. Also included, is an aqueous pharmaceutical carrier comprising at least two solvents selected from PEG-300, propylene glycol, polyvinyl pyrrolidone, polyvinyl alcohol, carbapol, and Laurocapram.

Also provided is a method of imaging myelin basic protein in an open or minimally invasive surgical field by topical administration of a pharmaceutical agent by contacting the surgical site with a pharmaceutical agent. The agent comprising a compound of Formula I or a salt thereof, wherein Formula I is:

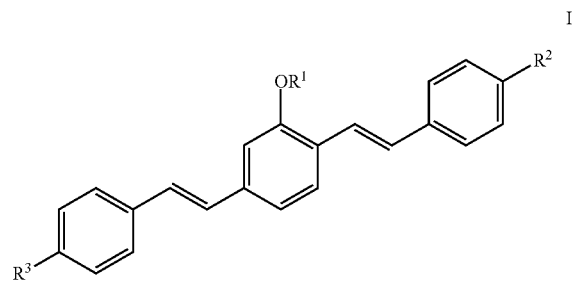

wherein R1 is an alkyl group, R2 is an electron donating group and R3 is an electron withdrawing group, and also comprising an aqueous pharmaceutical carrier. The method further comprises the step, after application, of detecting the agent by applying a light source tuned to the spectral excitation characteristics of the agent, and observing the subject through an optical filter tuned to the spectral emission characteristics of the agent.

Also provided are kits for providing a topical administered pharmaceutical agent described above.

BRIEF DESCRIPTION OF THE FIGURES

These and other features, aspects, and advantages of the present invention will become better understood when the following detailed description is read with reference to the accompanying figures wherein.

DETAILED DESCRIPTION

Figure 1:
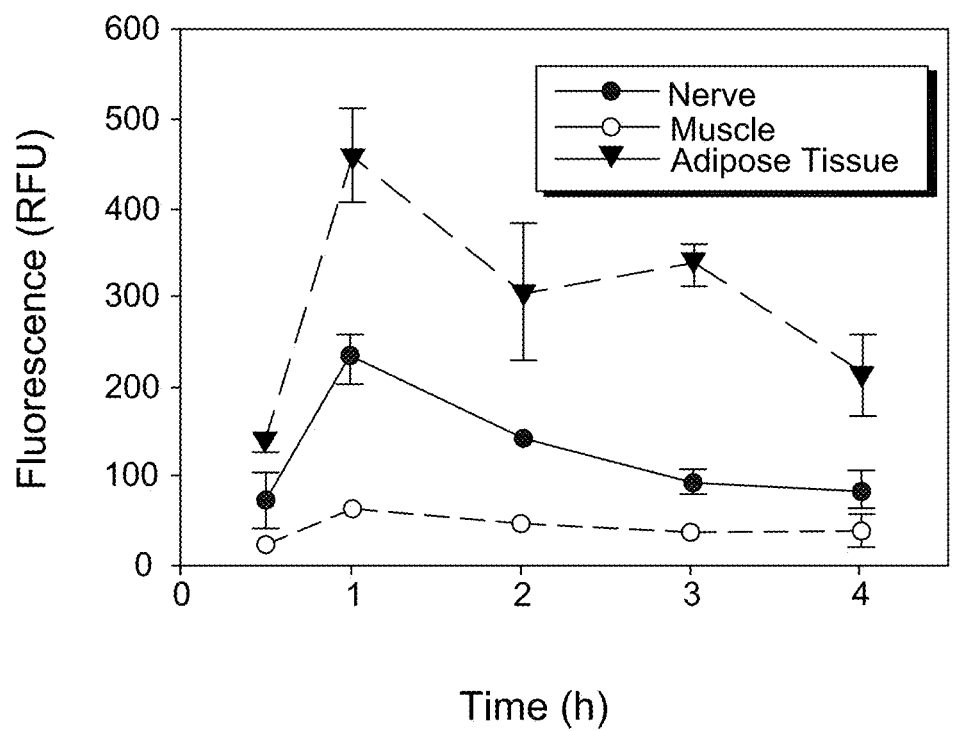
FIG. 1 shows the kinetics of uptake and clearance of IV injected FORMULA I(F) FORMULA I(f) in a murine model.

The following detailed description is exemplary and not intended to limit the invention of the application and uses of the invention. Furthermore, there is no intention to be limited by any theory presented in the preceding background of the invention or descriptions of the drawings.

To more clearly and concisely describe and point out the subject matter of the claimed invention, the following definitions are provided for specific terms, which are used in the following description and the appended claims.

"Myelin-associated neuropathy" generally refers to any condition in which the insulating material ensheathing portions of neuronal cells becomes damaged or dysfunctional as a component of a syndrome, disease, or other pathological condition, such as, but not limited to, multiple sclerosis, Guillain-Barré syndrome, leukodystrophies, metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy induced neuropathy, Alzheimer's disease, vascular dementia, dementia with Lewy bodies, or any combination thereof.

"Agent" refers to a solution or carrier for introducing a compound into a subject in a manner to allow the compound to be administered at a desired concentration and efficacy. The agent may include, but is not limited to, solvents, stabilization aids, buffers, and fillers. A pharmaceutical agent refers to the agents having medicinal or other biological properties including, but not limited to, use in therapy or diagnostics.

An agent exhibits "specific binding" for myelin if it associates more frequently with, more rapidly with, for a longer duration with, or with greater affinity to, myelin than with tissues not containing myelin. "Non-specific binding" refers to binding of the agent to non-myelin containing tissue. For relative binding values, such as specific binding or non-specific binding, each sample should be measured under similar physical conditions (i.e., temperature, pH, formulation, and mode of administration). Generally, specific binding is characterized by a relatively high affinity of an agent to a target and a relatively low to moderate capacity. Typically, binding is considered specific when the affinity constant $K_a$ is at least $10^6 \, M^{-1}$. A higher affinity constant indicates greater affinity, and thus typically greater specificity. For example, antibodies typically bind antigens with an affinity constant in the range of $10^6 \, M^{-1}$ to $10^9 \, M^{-1}$ or higher. "Non-specific" binding usually has a low affinity with a moderate to high capacity. Non-specific binding usually occurs when the affinity constant is below $10^6 \, M^{-1}$. Controlling the time and method used to contact the agent with the tissues reduces non-specific binding.

"Washing" generally refers to any method, such as but not limited to, immersion in, or flushing by repeated application of, a non-labeling solution or other substance, such as but not limited to water, saline, buffered saline, or ethanol, so as to provide a medium for dissociation, dispersal, and removal of unbound or non-specifically bound labeling compound from non-myelinated components of the tissue or sample of tissue without eliminating specific binding to myelin.

"Baseline fluorescence" refers to the frequency and magnitude of electromagnetic radiation emitted by a tissue or sample of tissue upon being exposed to an external source of electromagnetic radiation in the absence of administration or binding of any fluorescing compound, as distinguished from the radiation emitted following the administration and binding of such fluorescing compound and exposure to an external source of electromagnetic radiation.

"Control sample representative of the tissue section" refers to a tissue sample of a similar size, morphology, or structure as the tissue sample to be analyzed, and with a level of myelin whereby the sample's level of myelin serves as a reference to which other samples' myelin levels may be compared.

"Pharmaceutical carrier" refers to a composition, which allows the application of the agent material to the site of the application, surrounding tissues, or prepared tissue section to allow the agent to have an effective residence time for specific binding to the target or to provide a convenient manner of release. Solubilization strategies may include but are not limited to pH adjustments, salt formation, formation of ionizable compounds, use of co-solvents, complexation, surfactants and micelles, emulsions and micro-emulsions. The pharmaceutical carrier may include, but is not limited to, a solubilizer, percutaneous enhancers, detergent, buffer solution, stabilizers, and preservatives. Examples of these include but are not limited to, HCl, citric acid, DMSO, propylene glycol, ethanol PEG 300, cyclodextrins, citrate, acetate, phosphate, carbonate or tris(hydroxymethyl)aminomethane. An example of a percutaneous enhancer is Laurocapram which is capable of also transporting or carrying a compound across a barrier such as a transdermal penetration.

"Demyelination model" refers to any experimentally-induced damage to, or dysfunction of, the insulating material ensheathing portions of neuronal cells, that may be utilized in the experimental study of neuropathic demyelination, including, but not limited to, experimental allergic encephalomyelitis.

"Remyelination" refers to the spontaneous, therapeutic, or experimentally induced repair, regeneration, or otherwise enhanced constitution or functionality of the insulating material ensheathing neuronal axons.

"Alkyl" is intended to include linear, branched, or cyclic hydrocarbon structures and combinations thereof, including lower alkyl and higher alkyl. Alkyl groups are those of C20 or below. "Lower alkyl" refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

"Substituted" refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

"Electron donating group" refers to chemical groups that add electron density to the conjugated π system making it more nucleophilic. Electron donating groups may be recognized by lone pairs of electrons on an atom adjacent to the π system. Examples of electron donating groups include, but are not limited to, —NR'R", —NHR, —$NH_2$, —$NC(NH_2)_2$, —OH, —OR, —SR, —NHCOR, —OCOR, —$C_6H_5$, and —CH=$CR_2$.

"Electron withdrawing group" refers to chemical groups that remove electron density from the conjugated π system rendering the structure less nucleophilic. Electron withdrawing groups may be recognized either by the atom adjacent to the π system having several bonds to more electronegative atoms or, having a formal positive charge. Examples of electron withdrawing groups include, but are not limited to, —CHO, —COR, —COOR, —COOH, —$CONH_2$, —CONHR, —$CONR_2$, —$CF_3$, —CN, C=$C(CN)_2$—$SO_3H$, —$NH_3+$, —$NR_3+$, —$NO_2$, —SOR, —$SO_2R$, —$SO_2NH_2$, —$SO_2NHR$, and —$SO_2NR_2$.

An agent exhibits "specific uptake" for myelinated tissues if it associates more frequently with, more rapidly with, for a longer duration with, or with greater affinity to, or if it is absorbed more, or accumulates more in myelinated tissues than with non-myelinated tissues. Generally, specific uptake is characterized by a relatively high affinity of an agent to a target.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Many of the compounds described herein may comprise one or more asymmetric centers and may thus give rise to enantiomers, diastereomers, and other stereoisomeric forms that may be defined, in terms of absolute stereochemistry, as (R)- or (S)-. The chemical structure of the agent includes for example, without limitation, all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also included.

In certain embodiments, a method for the qualitative or quantitative detection of myelin basic protein through topical application of an agent that specifically binds to myelin basic protein is provided. The specific binding to myelin basic protein may be by an a compound of Formula I or its salt

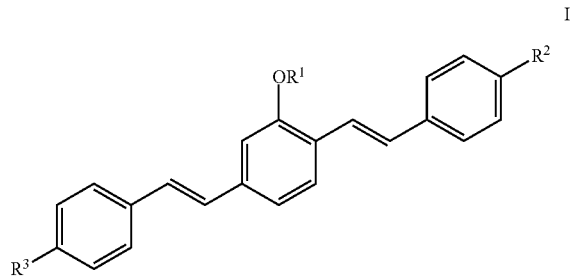

wherein $R^1$ is an alkyl group, $R^2$ is an electron donating group and $R^3$ is an electron withdrawing group.

In certain embodiments $R^1$ be a lower alkyl groups of from 1 to 6 carbon atoms, preferably from 1 to 4 carbon atoms, and includes methyl, ethyl, n-propyl, isopropyl, and n-, s- and t-butyl. The electron-donating group, $R^2$, may include a primary, secondary, or tertiary amine, or an alkoxy group. Preferably, $R^2$ may be an amine, and more preferably $NH_2$.

In certain preferred embodiments, the specific binding to myelin basic protein may be by an a compound of Formula I(a) or its salt

I (a)

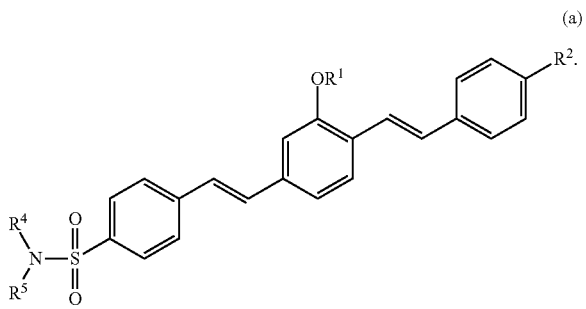

wherein $R^4$ and $R^5$ may be used to improve aqueous solubility and reduce log P of the agent. $R^4$ and $R^5$ may be independently a hydrogen atom or an alkyl, preferably a lower alkyl group of from 1 to 6 carbon atoms. In other embodiments, $R^4$ and $R^5$ may independently be a substituted alkyl groups, such as, but not limited to an alkoxy or alcohol. In certain embodiments, the alkoxy group may contain ethylene glycol units or an ethylene glycol terminated alcohol; for example $(CH_2CH_2O)_nX$ or $CH_2CH_2CH_2(OCH_2CH_2)_nOX$ where n is an integer between 1 and 6 and X is hydrogen, methyl or ethyl. In still other embodiments, when $R^4$ and $R^5$ form an unsubstituted or substituted heterocyclic ring structure. The heterocyclic ring structure may be piperidine, piperazine, or morpholine or an alkyl or alkoxyl substituted piperidine, piperazine, or morpholine.

In each embodiment, $R^2$ and the sulfonamide group $R^4R^5NSO_2$ are conjugated through the π double bond orbitals of the benzene rings and olefinic substituents, thereby providing a clear path for electrons to flow from the electron-donating group to the electron-withdrawing group.

In certain embodiments, the agent may be a salt of Formula I, wherein $R^4$ and $R^5$ may comprise an ammonium cation with an anion. The ammonium salt may be a tertiary ammonium salt wherein the anion may be a halide. In other embodiments, the anion may be polyatomic such as, but not limited to nitrate, carbonate, sulfate, and phosphate. The polyatomic anion may also comprise a halide such as, but not limited to, a tetrafluoroborate, hexafluorophosphate, a fluoropolyphosphate, or a combination thereof. In still other examples, the anion may originate from carboxylic acids, such as, but not limited to, citrate, tartrate, maleate, malate, fumarate, itaconate, or ascorbate. For in vivo applications, those anions with low biological toxicity would be preferred.

Other non-limiting examples of Formula I, are shown in Table 1 (Formula I (b-f)).

TABLE 1

Formula I b

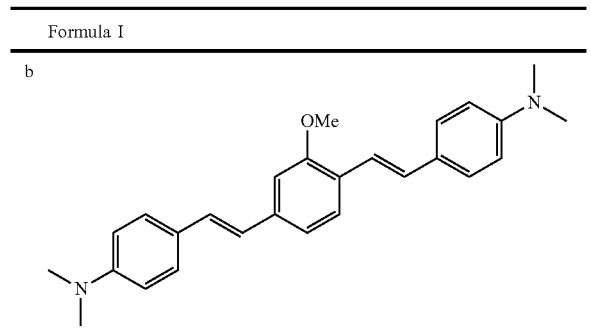

TABLE 1-continued

Formula I

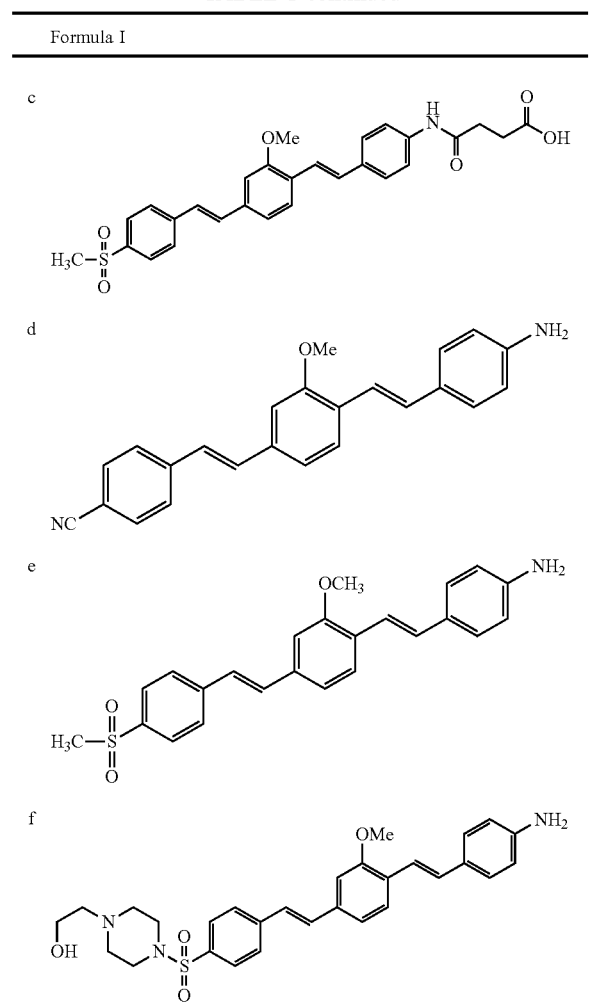

In certain embodiments, agents, which have improved aqueous solubility compared to similar agents, may lessen nonspecific partitioning of the agents to the non-target tissue, such as adipose tissue. Also, improved aqueous solubility may enable the agents to be formulated in pharmaceutical carriers with less or no known toxic effects, thus making them more suitable for use in higher dosage and providing researchers and clinicians important diagnostic and treatment tools.

In certain embodiments, a light source tuned to the spectral excitation characteristics of the agent may be applied to the area of application. The agent may be observed through an optical filter tuned to its spectral emission characteristics. Due to their specific binding to the fluorescing agent, nerves and other myelin containing tissue are distinguishable from tissue not containing myelin basic protein. This enables the surgeon to avoid inadvertently cutting or damaging myelinated tissue by avoiding fluorescing tissue, or facilitates accurately administering treatment to the intended myelinated tissue.

In certain embodiments, the pharmaceutical agent may be specially formulation and can be locally applied as solutions, powders, gels, emulsions, creams, ointments, beads or collagen implants.

After topical administration, a light source tuned to the spectral excitation characteristics of the agent may be applied to the application field. The agent may be observed through an optical filter tuned to its spectral emission characteristics. Due to their specific binding to the fluorescing agent, nerves and other myelin containing tissue are distinguishable from tissue not containing myelin basic protein. This enables, for example, a surgeon to avoid inadvertently cutting or damaging myelinated tissue by avoiding fluorescing tissue, or facilitates accurately administering treatment to the intended myelinated tissue. In certain embodiments, the agent comprises the compound of Formula I.

To determine whether myelination in the patient may be deficient, myelination levels may be compared to those exhibited by a subject or subjects believed or known not to be suffering from a myelin-associated neuropathy. In another embodiment, rates of demyelination or remyelination may be determined. Following treatment with a known or suggested therapeutic agent believed or anticipated to prevent or slow demyelination or to promote remyelination in patients suffering from myelin-associated neuropathies, myelination levels are evaluated by performing the imaging over time in the patients treated with the therapeutic agent. The imaging may be performed at different points of time and the level of myelination at one time point compared to that of another. As such, level of myelination may be determined qualitatively or quantitatively.

After binding to myelin basic protein, the sample may be washed in a manner and medium suitable to remove any unbound and non-specifically bound label from the sample, without eliminating specific binding to myelin basic protein.

In certain embodiments, a pharmaceutical carrier may be used to enhance, at least one of, solubility, penetration or bioavailability of an agent comprising a compound of Formula I or its salt. In certain embodiments the pharmaceutical carrier may be used to enhance the solubility of the compound in a solution as well as acting to carry or transport the compound across a barrier, for example to allow for percutaneous penetration.

In certain embodiments, the pharmaceutical carrier may comprise carbopol, polyethylene glycol (such as PEG-300), propylene glycol, polyvinyl alcohol, polyvinyl pyrrolidone, or Laurocapram, for intraoperative local administration.

In certain embodiments, the pharmaceutical carrier is an aqueous solution comprising 1-30% PEG-300, 1-20% propylene glycol, 1-10% polyvinyl pyrrolidone, and 0-10% Laurocapram based on volume.

In certain embodiments, the pharmaceutical carrier is an aqueous solution comprises 20% PEG-300, 10% propylene glycol, 5% polyvinyl pyrrolidone, and 5% Laurocapram, based on volume.

Other pharmaceutical carriers may include, but are not limited to, surfactants including non-ionic surfactants, lipids including triglycertides, cyclodextrins, and phospholipids as well as other detergents, buffer solutions, stabilizers, and preservatives. In each case, the use of both water-soluble and water-insoluble organic solvents may be used in combination with other pharmaceutical carriers to limit the occurrence of precipitation, pain, inflammation and homolysis upon administration.

Techniques to enhance solubility of the agent may include, pH adjustment, salt formation as described above co-solvents, complexation, emulsions, micelles, and liposomes. The pharmaceutical carrier may also include, but is not limited to, surfactants such as a detergent, buffer solutions, stabilizers, and preservatives. In certain embodiments, the carrier may also include a percutaneous enhancer which acts to carry a compound or drug across a barrier including transdermal delivery.

In certain embodiments, an agent comprising, a compound of Formula I or its salt may be packaged and provide in the form of a kit that ensures sterility of the agent is maintain as well as other critical parameters such as pH, solubility, and concentration. The kit would comprise the agent in, in a form suitable for administration such as dissolved in a pharmaceutical carrier. In certain embodiments, the pharmaceutical carrier may further comprise co-solvent, surfactant, buffer solution, stabilizer, and preservative, or a combination thereof for proper storage or handling of the agent.

In certain embodiments, the kit may be configured as a multi-chambered vessel for storing the pharmaceutical agent in a first chamber and the pharmaceutical carrier in a second chamber. In certain embodiments, the pharmaceutical agent may be stored in a first chamber with a pharmaceutical carrier and optionally buffer solution, stabilizer, and preservative, or a combination thereof. The second chamber may contain other components of the pharmaceutical carrier to enhance solubility prior to application. As such, the components of the carrier may be desirable for application of the agent, as intended, but is detrimental for storage or long-term stability of the agent.

EXAMPLES

The following non-limiting examples are shown and describe various embodiments of the present invention. The examples include data acquired comparing systemically administered contrast agents with local intraoperative application of nerve labeling contrast agents. As shown it demonstrates that when properly formulated, topically applied nerve labeling contrast agent can selectively label nerves within a much quicker time, with lower dosage, and with better nerve-to-muscle contrast compared to systemically administered nerve labeling agent. In vitro characterization of contrast agents:

Absorbance spectra of the agents were measured using a Lambda 20 UV/Vis spectrometer (Perkin Elmer, Waltham, Mass.) in wavelengths ranging from 200-to-800 nm in 100% dimethylsulfoxide (DMSO), absolute methanol (MeOH), and distilled/deionized water (ddH2O). The wavelength of maximum absorbance was then used as the excitation wavelength for the collection of the fluorescence emission spectra on a steady state fluorimeter (Photon Technology International, Birmingham, N.J.).

Ex Vivo Labeling of Nerves:

Various nerves were harvested from male Sprague Dawley rats. Tissue was fixed by perfusion and post-fixed with 10% neutral buffered formalin. Following post-fixation, tissue was cryoprotected in a 20% sucrose solution made in phosphate buffered saline (PBS). Nerves were then flash-frozen using methanol and dry ice in OCT media. In some cases, polyvinylidene fluoride membranes were used to help keep the nerves vertical in the OCT media. 5-10 micron section were sliced on a Leica microtome and stored in a −80° C. freezer prior to staining with agents (1)-(5).

For ex vivo staining of nerve sections, the slides were rinsed in PBS (3×5 min). Contrast agent (with a final concentration of 10 uM) was added onto the tissue in a buffer containing 10% Cremophor EL and 65% rat serum in PBS. The slides were incubated for 1 h in a dark, humid chamber after which they were washed with PBS (3×5 min), cover-slipped, and imaged using a custom filter cube (excitation filter: 387 nm with 11 nm band pass, 409 nm dichroic mirror; emission filter: 409 nm long pass). A buffer only control was also performed using exactly the same procedure to determine autofluorescence under the same settings.

In Vivo Imaging Instrumentation:

Commercial small animal system: A fluorescence stereomicroscope (SteREO Lumar V12, Carl Zeiss Inc., Thornwood, N.Y.) equipped with a multispectral imaging camera (Nuance, CRI, Woburn, Mass.) was used with an exposure time of 1-5 s. Excitation of the flurophores was achieved using a filter centered at 406 nm with a 15 nm bandwidth. The fluorescence emission spectrum was recorded at wavelengths ranging from 420 to 720 nm at 10-nm increments using the attached multispectral camera. Alternatively, we had also used an emission filter with 550 long pass filter (in the absence of multispectral camera).

Real-time intraoperative imaging was achieved with a dual-mode laparoscopic fluorescence imaging instrument. The laparoscope module comprises a standard 10 mm zero degree surgical laparoscope with 70 degree field of view, a 4 mm diameter, 1800 mm long laparoscope light guide, 35 mm video coupler, a compact 90 gram, 659×494 pixel GigE color camera (acA640-90gc Basler, Ahrensburg, Germany), and a 405 nm blocking filter (BLP01-405R Semrock, Rochester, N.Y.), which has >97% transmission from 420 to 800 nm. The ⅓" format sensor provides high sensitivity with 7.4 μm pixel size and adequate field of view (40 degrees out of 70 degrees passed by the laparoscope). The video coupler interfaces with the eyepiece of the laparoscope providing an interchangeable set up for different types of laparoscopes. The 405 nm filter is secured directly in front of the image sensor with a c-mount retaining ring. The camera threads onto the video coupler directly.

Illumination for white light and fluorescence imaging is coupled into a single light guide using conventional optics. The light coupling module consists of two 32 mm aspheric lenses to collimate a white light LED and a 500 mW, 405 nm blue laser diode coupled into a multimode fiber with 400 μm diameter (Shanghai Laser & Optics Century Co., Ltd., China). The LED spectrum is filtered with a 450 nm long pass filter (NT49-819, Edmund Optics, Barrington, N.J.) to minimize excitation of the fluorescent agent, while maintaining the white light color spectrum. The LED and laser are combined with a 425 nm dichroic mirror (DMLP425R, Thorlabs). The combined illumination is coupled into the light guide with a third 32 mm aspheric lens (ACL4532, Thorlabs). The maximum irradiance from the LED and 405 nm laser are 2.0 mW/cm2 and 7.3 mW/cm2, respectively, at 25 mm from the tip of the laparoscope.

Formulation, Dosing, and Kinetics for In Vivo Imaging Following Systemic IV Injection of Contrast Agent in Animal Model:

For systemic administration by IV injection, the contrast agents were formulated using the following excipients: 5-15% propylene glycol (Fisher P355-1), 5-30% 2-hydroxypropyl-β-cyclodextrin (2-HPβCD, Sigma H5784) and 70-90% distilled/deionized water. In some cases, PEG-300 and DMSO were also added. The IV formulation was brought to a final pH of 7.4 using 1M of hydrochloric acid. Complete solubility of FORMULA I(f) in the formulation was verified using (1) visual observation for particulates, (2) centrifugation (5 min at 12,000 g) followed by observation, (3) dissolution in a physiologically relevant buffer (e.g., Sorenson's phosphate buffer) followed by visual observation and UV/Vis analysis, and (4) assessment of sedimentation and particle size using dynamic light scattering.

Specifically, IV formulation for FORMULA I(f) consisted of 80% distilled/deionized water, 10% 2-hydroxypropyl-β-cyclodextrin (2-HPβCD, Sigma H5784), and 10% propylene glycol (Fisher P355-1).

For the murine studies, CD-1 mice ranging in body weight from 25 to 30 g, and Sprague-Dawley rats ranging in body weight from 250 to 300 g, were purchased from Charles River Laboratories (Wilmington, Mass.). On the day of the experiment, mice or rats were anesthetized using 2%-4% isofluorane and given a single tail vein injection each of IV formulated FORMULA I(F) at 16 mg/kg. The animals were then returned to the home cage until the designated timepoint for imaging.

Formulation and Dosing for Intraoperative Topical Administration:

Several different formulations were tested, including but not limited to:

Formulation 1: 10% PEG-300; 20% PG; 0.4% Carbopol; 69.6% water;

Formulation 2: 10% DMSO; 20% PEG-800; 20% PG; 0.1% Polysorbate-80; 49.9% Water;

Formulation 3: 30% PEG-300; 5% DMSO; 10% PVA; 55% water;

Formulation 4: 30% PEG-300; 10% PVA; 60% water;

Formulation 5: 30% PEG-300; 5% DMSO; 30% Pluronic F-68; 0.1% Polysorbate-80; 34.9% water;

Formulation 6: 20% PEG-300; 10% PG; 5% PVP; 5% Laurocapram; 60% water;

Formulation 7: 20% PEG-300; 10% PG; 5% PVP; 5% Laurocapram; 5% EtOH; 5% oleic acid; 10% Tween-80; 40% water;

where: PVA=polyvinyl alcohol; PVP=polyvinyl pyrrolidone; and PEG=polyethylene glycol.

Various amounts of powdered contrast agent, were formulated into the above excipients. The solution or gel was applied into the surgical site in the murine model, with contact time ranging from less than 1 minute to 20 minutes. The surgical site was then irrigated with wash solution, such as warm saline, and the animals were imaged.

For the porcine imaging studies, pigs were sedated with tiletamine/zolazepam (4.4 mg/kg), given glycopyrrolate (0.007 mg/kg), and a local infiltrate of bupivacaine (0.25%) was delivered subcutaneously along the midline prior to laparotomy. Pig was intubated and maintained on isoflurane (1.5%-2.5%) during the surgery. A 16-gauge angiocatheter was placed in an ear vein for blood collection and drug administration. Normosol-R was given at a rate of 10-15 mL/kg/h during the procedure. Continuous monitoring of vital signs, temperature, and oxygenation was performed to assure the pigs' safety and health. The solution or gel was applied into the surgical site with contact time ranging from 1 minute to 5 minutes. The surgical site was then irrigated with warm saline, and the surgical sites were imaged.

FIG. 1 shows the kinetics of uptake and clearance of IV injected FORMULA I(f) in a murine model. A dose of 16.6 mg/kg of FORMULA I(f) was used for measuring the nerve fluorescence at 0.5, 1, 2, 3 and 4 hours after IV injection. Maximum sciatic nerve and adipose tissue fluorescence were observed at 1 h post injection and decreased rapidly through subsequent time points. The best nerve-to-muscle ratio observed at 1 h post-injection, with a value of 3.7.

Figure 2A:
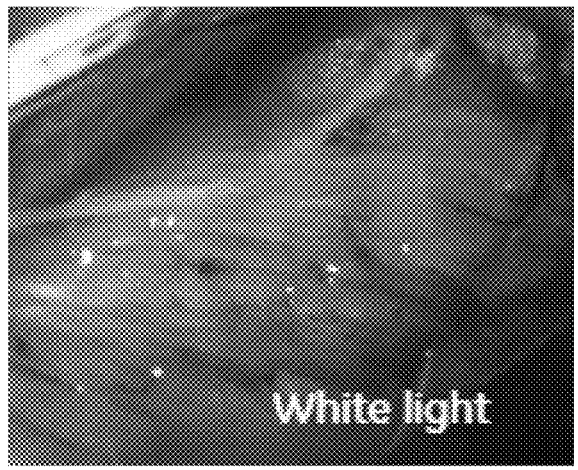
FIG. 2A is a representative white light image from nerves after intraoperative topical application of FORMULA I(f) in a murine model.
Figure 2B:
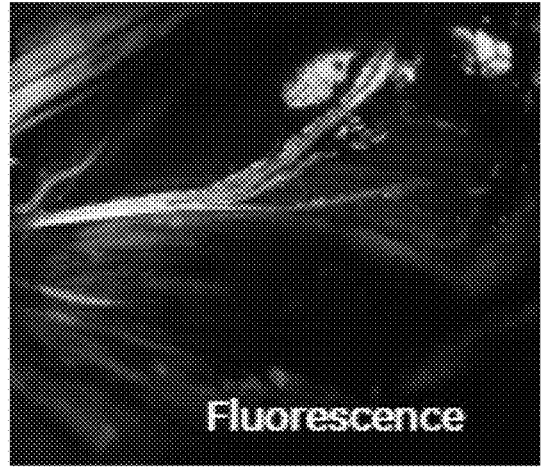
FIG. 2B is the same murine model as FIG. 2A and is a representative fluorescence image from nerves after intraoperative topical application of FORMULA I(f) in a murine model.

Topically administered nerve labeling dyes were also able to label nerves in a living animal. The fluorescence from nerves can be detected within minutes after intraoperative topical application. Representative white light and fluorescence images of topically administered FORMULA I(f) in a mouse are shown in FIG. 2A (white light) and FIG. 2B (fluorescence). When visualized using the intraoperative dual-model laparoscopic instrument, very fine nerve fibers in a brachial plexus branch of a murine model were more readily detected under fluorescence guidance. In this example, FORMULA I(f) in Formulation 4 was applied at the brachial plexus surgical site of a mouse for 5 minutes, and then the area was irrigated with sterile saline prior to imaging.

Figure 2C:
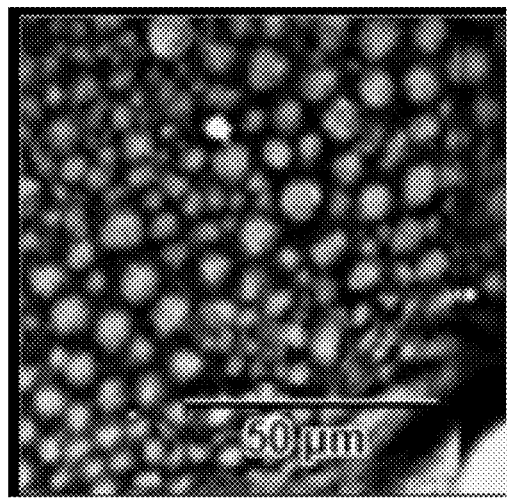
FIG. 2C is a fluorescence microscopy image showing donut-shaped myelin bundles are stained with FORMULA I(f) following intraoperative topical application in a murine model.

FIG. 2C shows that similar to IV injected contrast agent, topically applied contrast agent can penetrate into the nerve bundle. Following topical application, irrigation, and excision of the sciatic nerve in a murine model, the nerve tissue was cryosectioned into 15 micron thick sections. Fluorescence microscopy imaging showed that the donut-shaped myelin bundles were stained with the fluorophore.

Figure 2D:
FIG. 2D is a microscopy image showing fluorescence nerve labeling in a mouse by topically applied FORMULA I(d).

FIG. 2D shows fluorescence nerve labeling in a mouse by topically applied FORMULA I(d), a compound related to FORMULA I(f) in its core structure. Imaging was performed using a small animal commercial instrument.

Figure 3:
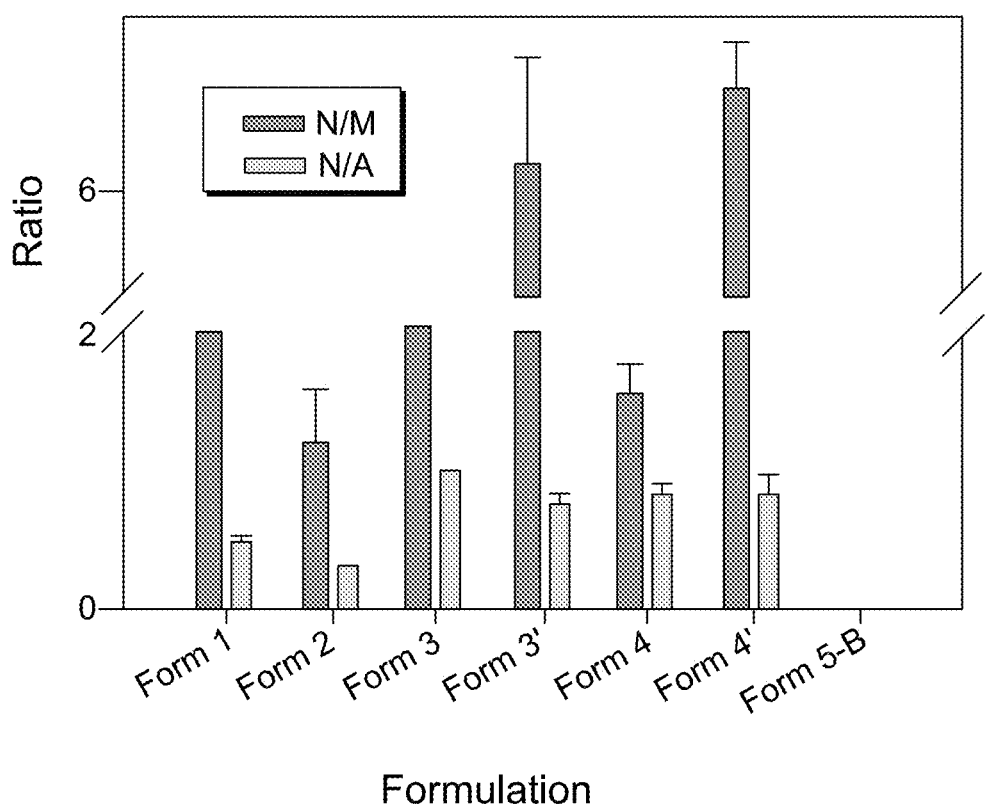
FIG. 3 is a graph comparing the relative nerve-to-muscle (N/M) and nerve-to-adipose tissue (N/A) ratios of FORMULA I(f) formulated in different pharmaceutical carriers when applied topically at the surgical site in a murine model.
Figure 4:
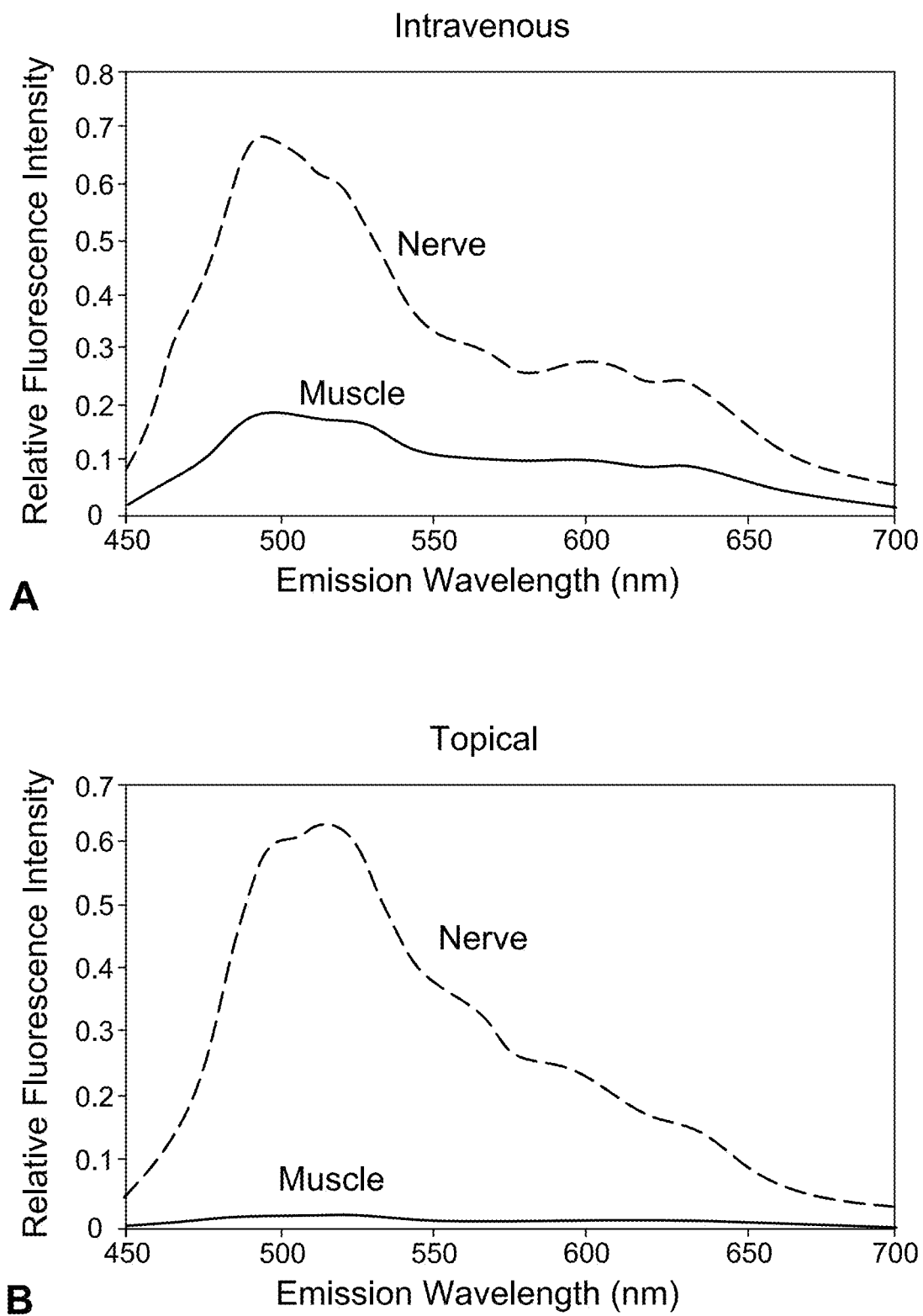
FIG. 4 is multispectral imaging plots comparing the contrast between systemically (intravenously) administered FORMULA I(f) (graph A) with topically applied FORMULA I(f) in a murine model (graph B).

FIG. 3 shows the relative nerve-to-muscle (N/M) and nerve-to-adipose tissue (N/A) of topically applied FORMULA I(f) when applied at the surgical site in the murine model, comparing different pharmaceutical carriers for intraoperative topical application. FORMULA I(f) was formulated in different ways as described above. The different formulations affected the contrast between the nerves and the surrounding tissue. For example, Formulation 6 and Formulation 4 demonstrated the best contrast between nerve-to-muscle and nerve-to-adipose tissue. Each of the formulation components were added to render to affect the (a) solubilization of the agent, (b) the stability of the formulated agent, (c) viscosity of the formulated agent to enhance exposure of the surgical site, (d) the penetration of the agent within the surgical site, and (e) specific signal and non-specific background fluorescence. About 70 micrograms of formulated FORMULA I(f) was applied at the surgical site for about 1 minute, followed by washing with saline Topically administered nerve labeling agents can further produce clearer images, as a result of, lower non-specific fluorescence from surrounding non-target tissue (such as muscle). FIG. 4 shows multispectral imaging plots comparing the contrast between systemically (intravenously) administered FORMULA I(f) (FIG. 4A) with topically applied FORMULA I(f) (FIG. 4B) in a murine model. The total dose required for visualization in a given surgical site was less for topically administered contrast agent. In this example, the IV injected dose of FORMULA I(f) was about 16 mg/kg (0.4 milligrams for a typical mouse). The topically administered dose was about 0.1 milligrams in Formulation 4. FIG. 4 shows the nerves were clearer to visualize under topically administered agent because fluorescence intensity from the surrounding muscle tissue was lower across all the emission wavelengths compared to the systemically administered contrast agent.

Figure 5:
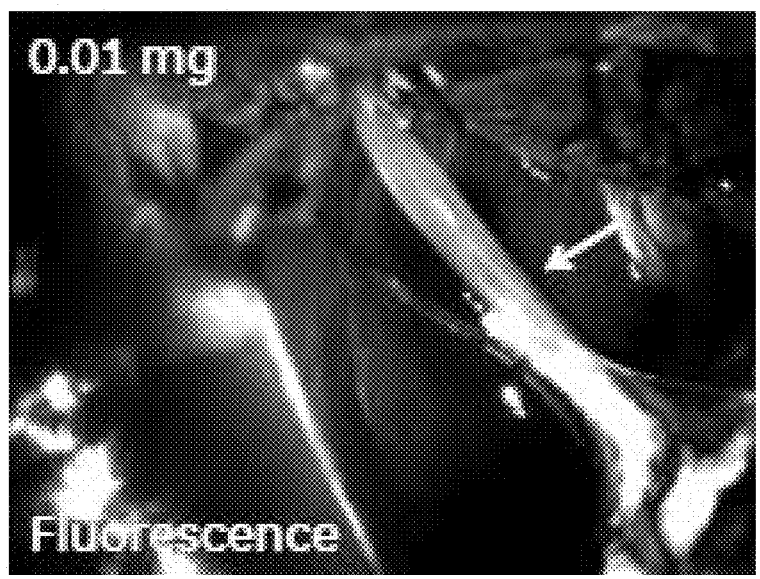
FIG. 5 are fluorescence images of 0.01 milligrams (A) and 0.02 milligrams (B) of FORMULA I(f) in Formulation 6 applied topically at the surgical site.
Figure 5:
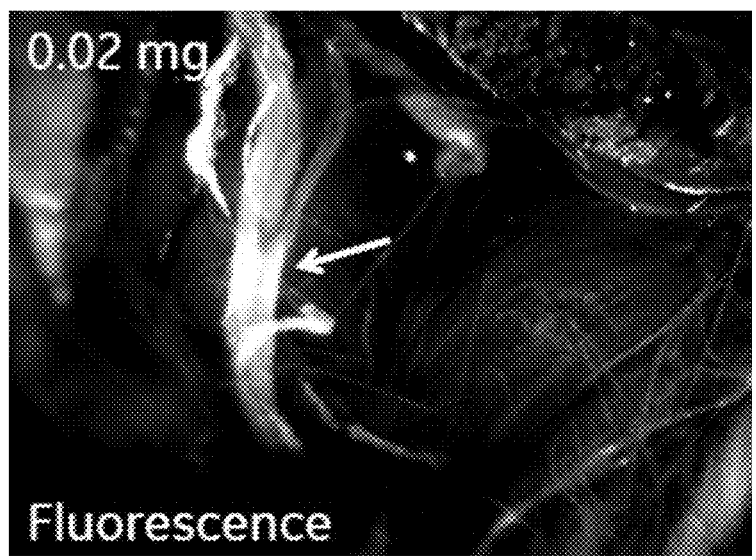

The intraoperative topical dose can be applied at a much lower concentrations. Dose as low as 0.01 mg can effectively visualize fluorescent nerves in a mouse model. In FIG. 5, 0.01 or 0.02 milligrams of FORMULA I(f) in Formulation 6 was applied topically at the surgical site, incubated for 3 minutes and then immediately irrigated with saline.

Figure 6A:
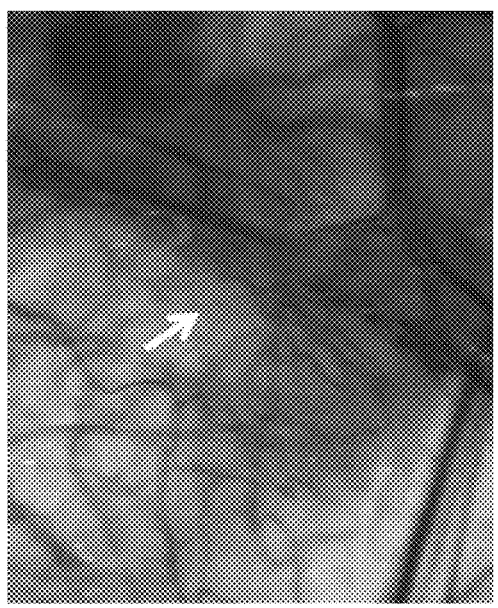
FIG. 6A are frames extracted from the real-time intraoperative imaging video showing white light and fluorescence images of 4 milligrams of FORMULA I(f) in Formulation 4 applied topically to a porcine surgical model; the nerve was not at all visible under white light imaging, while it was highly detectable under fluorescence guidance (arrow in the two panels)
Figure 6A:
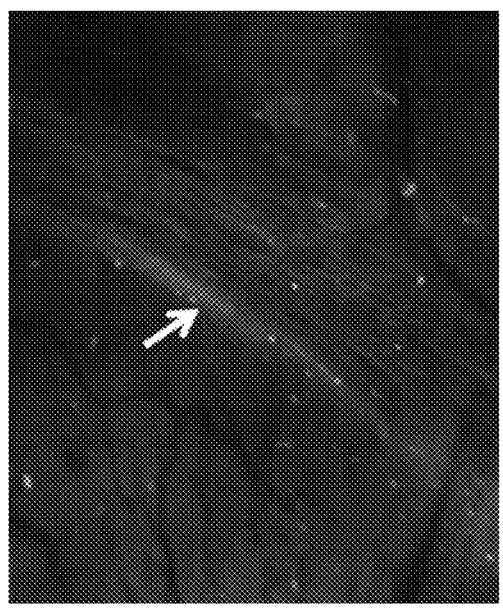
Figure 6B:
FIG. 6B are frames extracted from the real-time intraoperative imaging video showing white light and fluorescence images of 0.3 milligrams of FORMULA I(f) in Formulation 6, applied to surgical site around the retroperitoneal area; at lower dosage, the nerve (arrow) was more pronounced under fluorescence imaging compared to white light imaging.
Figure 6B:
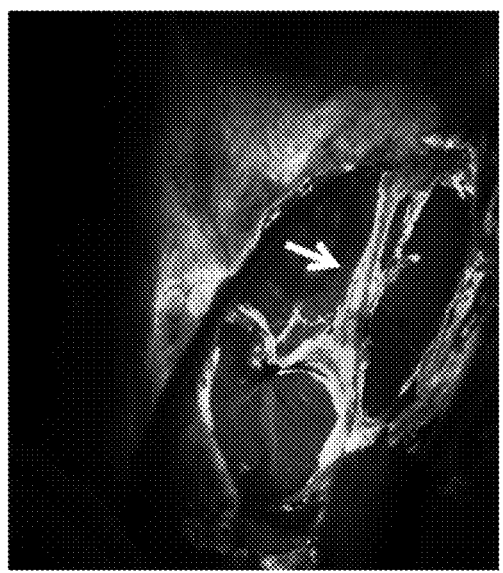

Scaling to a larger animal, topically administered FORMULA I(f) was also tested in a porcine surgical model. In FIG. 6A, 4 milligrams of FORMULA I(f) in Formulation 4 was applied into the surgical field, incubated for 5 minutes, and then irrigated with warm saline. The nerve was not at all visible under white light imaging, while it was highly detectable under fluorescence guidance (arrow in the two panels). In FIG. 6B, 0.3 milligrams of FORMULA I(f) in Formulation 6 was applied to the surgical site around the retroperitoneal area, then incubated for 3 minutes before irrigation with saline. Even at this lower dosage, the nerve (arrow) was more pronounced under fluorescence imaging compared to white light imaging. These intraoperative topical dosages in the pig model were far less than the typical dosage for systemic IV injection (typically between 30-50 milligrams of the nerve-labeling agent for a 35 kilogram pig).

Figure 7:
FIG. 7 are comparative fluorescence microscopy images of cryosectioned nerve tissue labeled with 10 uM of Formula I dyes (Ib-f), compared to control tissue which was incubated with buffer only. Scale bar ~50 microns.
Figure 7:
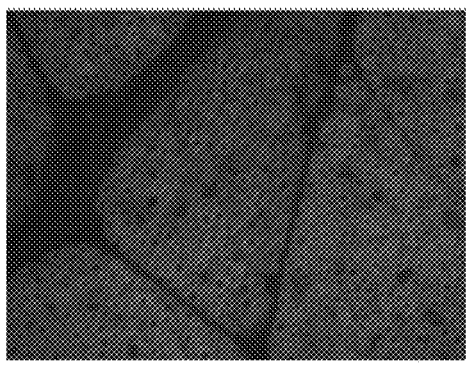
Figure 7:
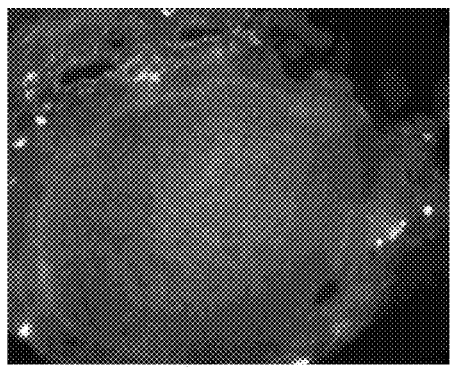
Figure 7:
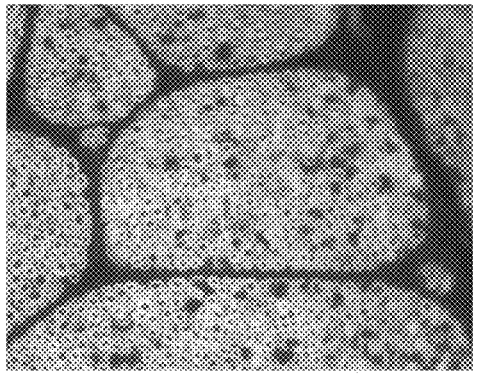
Figure 7:
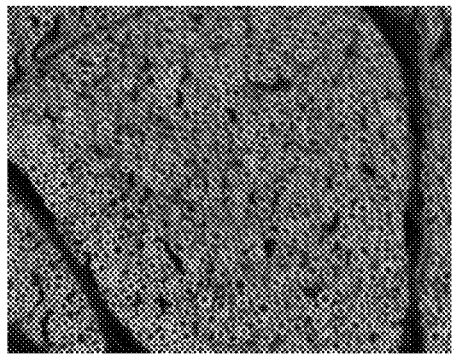
Figure 7:
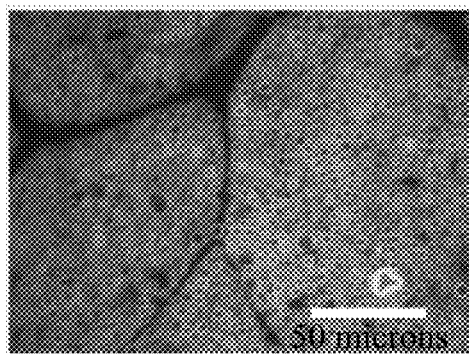

Intraoperative topical application of the nerve labeling dyes have been demonstrated for FORMULA I(f) and FORMULA I(d) in living animals. Molecules that are related to the "push-pull" core structure of this class of compound would also benefit from this new method of application. The following is an example of ex vivo labeling of resected nerve tissue. In here, compounds used to stain cryo sectioned nerve tissue from rats. FIG. 7 shows examples of microscopic images of fluorescently labeled rat nerve tissue sections. Here, the "push-pull" compounds (FORMULA I(f), FORMULA I(d), and FORMULA I(e)) exhibited the most robust fluorescent staining of nerve tissue sections.

While only certain features of embodiments have been illustrated and described herein, many modifications and changes will occur to those skilled in the art. It is, therefore, to be understood that the appended claims are intended to cover all such modifications and changes as falling within the spirit of the invention.

The invention claimed is:

1. A topical administered pharmaceutical agent comprising a compound of Formula I or a salt thereof, wherein Formula I is:

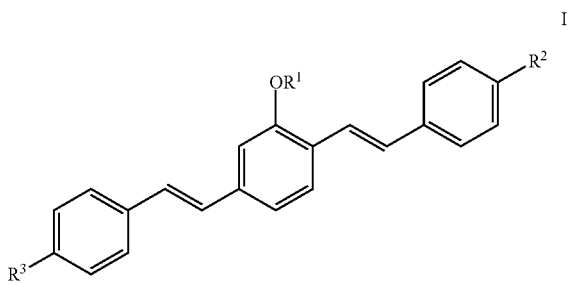

wherein $R^1$ is an alkyl group, $R^2$ is an electron donating group and $R^3$ is an electron withdrawing group; and an aqueous pharmaceutical carrier comprising, based on volume:

1-30% PEG-300, 1-20% propylene glycol, 1-10% polyvinylpyrrolidone, and 0-10% Laurocapram.

2. The pharmaceutical agent of claim 1, wherein the PEG-300 is 10-30% PEG-300 and wherein the aqueous pharmaceutical carrier further comprises 5-20% polyvinyl alcohol based on volume.

3. The pharmaceutical agent of claim 1, wherein $R^1$ is a lower alkyl group from 1 to 6 carbon atoms, and $R^2$ is a primary, secondary, or tertiary amine, or an alkoxy group.

4. The pharmaceutical agent of claim 1, wherein Formula I is:

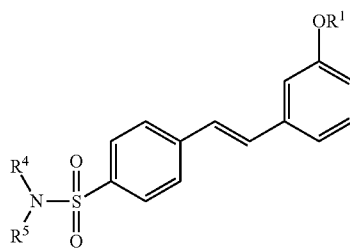

where $R^1$ is an alkyl group, $R^2$ is an electron donating group, and $R^4$ and $R^5$ are independently hydrogen, alkyl, substituted alkyl, amine, substituted amine, or taken together form a heterocyclic ring or substituted heterocyclic ring structure.

5. The pharmaceutical agent of claim 4, wherein the PEG-300 is 10-30% PEG-300 and wherein the aqueous pharmaceutical carrier further comprises 5-20% polyvinyl alcohol based on volume.

6. The pharmaceutical agent of claim 4, wherein $R^4$ and $R^5$ taken together form a heterocyclic ring or a substituted heterocyclic ring structure.

7. The pharmaceutical agent of claim 6, wherein $R^4$ and $R^5$ taken together form piperidine, piperazine, morpholine, or an alkyl or alkoxyl substituted piperidine, piperazine, or morpholine.

8. The pharmaceutical agent of claim 6 where Formula I is:

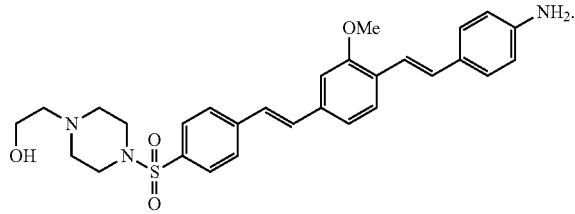 [SMILES: COc1cc(/C=C/c2ccc(S(=O)(=O)N3CCN(CCO)CC3)cc2)ccc1/C=C/c1ccc(N)cc1]

9. The pharmaceutical agent of claim 1, wherein Formula I is a salt further comprising an anion and said anion is a halide, a polyatomic anion, or a basic active compound.

10. The pharmaceutical agent of claim 9, wherein the anion is a chloride.

11. A method of imaging myelin basic protein in an open or minimally invasive surgical field by topical administration of a pharmaceutical agent comprising the steps of: contacting the surgical field with a pharmaceutical agent, said agent comprising a compound of Formula I or a salt thereof, wherein Formula I is:

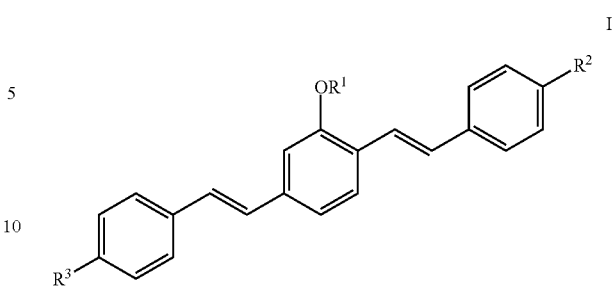

wherein $R^1$ is an alkyl group, $R^2$ is an electron donating group and $R^3$ is an electron withdrawing group; and an aqueous pharmaceutical carrier comprising, based on volume:

10-30% PEG-300 and 5-20% polyvinyl alcohol;

detecting the agent by applying a light source tuned to the spectral excitation characteristics of the agent; and observing a subject through an optical filter tuned to the spectral emission characteristics of the agent.

12. The method of claim 11, wherein the detecting is effected by fluorescence microscopy, laser-confocal microscopy, cross-polarization microscopy, autoradiography, or a combination thereof.

13. The method of claim 11, wherein $R^1$ is a lower alkyl group from 1 to 6 carbon atoms, $R^2$ is a primary, secondary, or tertiary amine, or an alkoxy group.

14. The method of claim 11, wherein Formula I is:

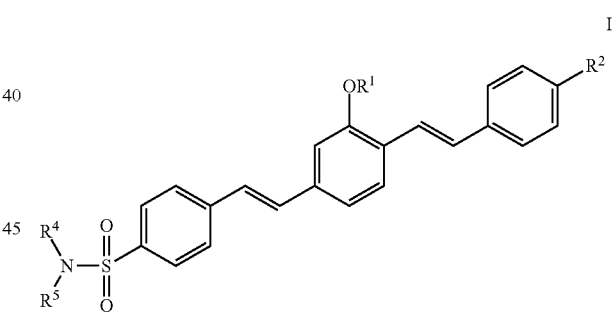

where $R^1$ is an alkyl group, $R^2$ is an electron donating group, and $R^4$ and $R^5$ are independently hydrogen, alkyl, substituted alkyl, amine, substituted amine, or taken together form a heterocyclic ring or substituted heterocyclic ring structure.

15. The method of claim 14, wherein the aqueous pharmaceutical carrier further comprises, based on volume:

1-20% propylene glycol, 1-10% polyvinyl pyrrolidone, and 0-10% Laurocapram.

16. The method of claim 14, wherein $R^4$ and $R^5$ taken together form a heterocyclic ring or a substituted heterocyclic ring structure.

17. The method of claim 16, wherein $R^4$ and $R^5$ taken together form piperidine, piperazine, morpholine, or an alkyl or alkoxyl substituted piperidine, piperazine, or morpholine.

18. The method of claim 17, where Formula I is:

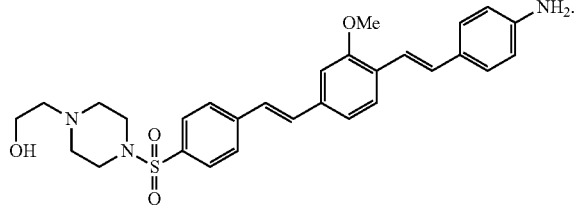 [SMILES: COc1cc(/C=C/c2ccc(S(=O)(=O)N3CCN(CCO)CC3)cc2)ccc1/C=C/c1ccc(N)cc1]

19. The method of claim 11, wherein Formula I is a salt further comprising an anion and said anion is a halide, a polyatomic anion, or a basic active compound.

20. The method of claim 19, wherein the anion is a chloride.

21. The method of claim 11, further comprising determining the presence of myelin based on spectral excitation of the agent.

22. A kit for providing a topical administered pharmaceutical agent comprising: a compound of Formula I or a salt thereof, wherein Formula I is:

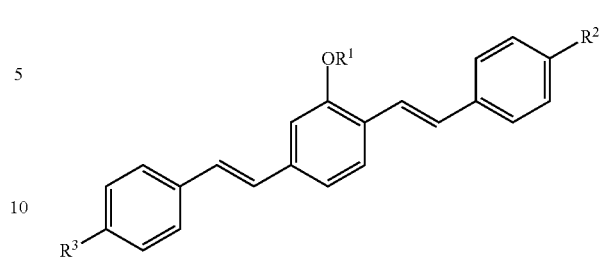

wherein $R^1$ is an alkyl group, $R^2$ is an electron donating group and $R^3$ is an electron withdrawing group;

an aqueous pharmaceutical carrier comprising, based on volume: 1-30% PEG-300, 1-20% propylene glycol, 1-10% polyvinylpyrrolidone, and 0-10% Laurocapram; and a co-solvent, surfactant, buffer solution, stabilizer, preservative, or any combination thereof.

23. The kit of claim 22, wherein the PEG-300 is 10-30% PEG-300 and wherein the aqueous pharmaceutical carrier further comprises 5-20% polyvinyl alcohol based on volume.

24. The kit of claim 22, wherein the pharmaceutical carrier further comprises a percutaneous enhancer, wherein the percutaneous enhancer comprises Laurocapram.

* * * * *